(12) United States Patent
Christensen et al.

(10) Patent No.: US 8,062,262 B2
(45) Date of Patent: Nov. 22, 2011

(54) EXTRAVASCULAR SYSTEM IN-LINE VENTING

(75) Inventors: Kelly D. Christensen, Centerville, UT (US); Wade A. Powell, Lexington, KY (US); John R. Stokes, Ogden, UT (US); Austin Jason McKinnon, Herriman, UT (US); Dinesh S. Kommireddy, Tarrytown, NY (US); Shaun Staley, Sandy, UT (US); Richard F. Leavitt, Layton, UT (US); Jesse Austin, Milliken, CO (US); Shaun Condie, Springville, UT (US); Tyler Evans, Provo, UT (US); Shawn Funk, Houston, TX (US); Scott Henderson, Logan, UT (US); Joseph Jacobsen, Pleasant Grove, UT (US); Austin Smith, Renton, WA (US); Christopher N. Cindrich, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 927 days.

(21) Appl. No.: 11/864,527

(22) Filed: Sep. 28, 2007
(Under 37 CFR 1.47)

(65) Prior Publication Data

US 2010/0057004 A1    Mar. 4, 2010

Related U.S. Application Data

(60) Provisional application No. 60/828,356, filed on Oct. 5, 2006.

(51) Int. Cl.
*A61M 5/00* (2006.01)

(52) U.S. Cl. .................................... 604/167.04

(58) Field of Classification Search ............. 604/164.01, 604/167.01, 167.02, 167.03, 167.04, 167.05, 604/167.06, 168.01, 122
See application file for complete search history.

(56) References Cited

U.S. PATENT DOCUMENTS

| | | | |
|---|---|---|---|
| 3,859,998 A | | 1/1975 | Thomas et al. |
| 4,193,399 A | | 3/1980 | Robinson |
| 4,193,400 A | | 3/1980 | Loveless et al. |
| 4,269,186 A | * | 5/1981 | Loveless et al. ........ 604/168.01 |
| 4,365,630 A | | 12/1982 | McFarlane |
| 4,444,203 A | * | 4/1984 | Engelman ................ 600/577 |
| 4,765,588 A | * | 8/1988 | Atkinson ................ 251/149.1 |
| 4,894,052 A | | 1/1990 | Crawford |
| 4,904,240 A | * | 2/1990 | Hoover ................ 604/508 |
| 4,917,671 A | | 4/1990 | Chang |
| 4,935,010 A | * | 6/1990 | Cox et al. ............. 604/122 |
| 4,966,586 A | | 10/1990 | Vaillancourt |
| 5,032,116 A | | 7/1991 | Peterson et al. |
| 5,049,130 A | * | 9/1991 | Powell ................ 604/103.05 |
| 5,066,284 A | * | 11/1991 | Mersch et al. ........ 604/168.01 |
| 5,226,883 A | | 7/1993 | Katsaros et al. |
| 5,242,411 A | * | 9/1993 | Yamamoto et al. ...... 604/167.04 |
| 5,295,969 A | | 3/1994 | Fischell et al. |
| 5,542,932 A | | 8/1996 | Daugherty |

(Continued)

*Primary Examiner* — Nicholas D Lucchesi
*Assistant Examiner* — Aarti B Berdichevsky
(74) *Attorney, Agent, or Firm* — Mony R. Ghose; Kirton & McConkie

(57) ABSTRACT

An extravascular system may include a fluid path and a gas vent in communication with the fluid path. A method of venting a medical device may include providing a closed extravascular system having a fluid path, providing a gas vent in communication with the fluid path, venting gas from the extravascular system through the gas vent, and maintaining closure of the extravascular system during and after venting.

28 Claims, 16 Drawing Sheets

U.S. PATENT DOCUMENTS

| | | | |
|---|---|---|---|
| 5,697,914 A | 12/1997 | Brimhall | |
| 5,749,857 A | 5/1998 | Cuppy | |
| 5,820,596 A * | 10/1998 | Rosen et al. | 604/108 |
| 5,824,001 A | 10/1998 | Erskine | |
| 5,980,492 A * | 11/1999 | Rosen et al. | 604/168.01 |
| 5,984,895 A | 11/1999 | Padilla et al. | |
| 6,171,287 B1 | 1/2001 | Lynn et al. | |
| 6,533,760 B2 | 3/2003 | Leong | |
| 6,533,770 B1 | 3/2003 | Lepulu et al. | |
| 6,638,252 B2 | 10/2003 | Moulton et al. | |
| 6,786,891 B2 | 9/2004 | Hiejima | |
| 2001/0047187 A1 * | 11/2001 | Milo et al. | 606/213 |
| 2003/0040760 A1 * | 2/2003 | Hnojewyj et al. | 606/148 |
| 2005/0015071 A1 | 1/2005 | Brimhall | |
| 2005/0027256 A1 * | 2/2005 | Barker et al. | 604/164.12 |
| 2008/0200903 A1 * | 8/2008 | Christensen et al. | 604/537 |
| 2008/0200904 A1 * | 8/2008 | Cluff et al. | 604/537 |
| 2008/0287906 A1 * | 11/2008 | Burkholz et al. | 604/500 |
| 2010/0042048 A1 * | 2/2010 | Christensen | 604/122 |

\* cited by examiner

EXTRAVASCULAR SYSTEM IN-LINE VENTING

RELATED APPLICATIONS

This application claims the benefit of U.S. Provisional Application No. 60/828,356, filed Oct. 5, 2006, entitled EXTRAVASCULAR SYSTEM IN-LINE VENTING, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously. One or more vascular or other devices used to access the vasculature of a patient are collectively referred to herein as an extravascular system.

One example of an extravascular system including a catheter is the BD NEXIVA™ Closed IV (intravenous) Catheter System, by Becton, Dickinson and Company. This system includes an over-the-needle, peripheral intravascular catheter made from polyurethane, another catheter used as an integrated extension tubing with a Y adapter and slide clamp, a vent plug, a Luer access device or port, and a passive needle-shielding mechanism.

The design of the BD NEXIVA™ IV catheter can be described as a closed system since it protects clinicians or operators from blood exposure during the catheter insertion procedure. Since the needle is withdrawn through a septum that seals, after the needle has been removed and both ports of the Y adapter are closed, blood is contained within the NEXIVA™ device during catheter insertion. The pressure exerted on the needle as it passes through the septum wipes blood from the needle, further reducing potential blood exposure. The slide clamp on the integrated extension tubing is provided to eliminate blood exposure when the vent plug is replaced with another vascular access device such as an infusion set connection or a Luer access device or port.

Following is a current procedure of initiating the use of an extravascular system such as the BD NEXIVA™ Closed IV Catheter System. A device operator will insert the needle into the vasculature of a patient and wait for flashback of blood to travel into the device to confirm that the needle is properly located within the vasculature of the patient. The blood travels into and along the catheter of the device because a vent plug permits air to escape the device as blood enters the device. After an operator confirms proper placement, the operator clamps the catheter to halt the progression of blood through the catheter, removes the vent plug, replaces the vent plug with another vascular access device such as an infusion set connection or a Luer access port, unclamps the catheter, flushes the blood from the catheter back into the vasculature of the patient, and re-clamps the catheter.

Many current procedures like the procedure described above present challenges that need to be overcome. For example, the procedure may include an unnecessary number of steps and amount of time to simply insert and prepare an extravascular system for use within the vasculature of a patient. Further, by removing the vent plug, the fluid path of the system is temporarily exposed to potential contamination from the external environment of the extravascular system.

Rather than using a vent plug, some operators attempt to solve the problem above by simply loosening a Luer access device and permitting air to escape from the system during flashback and then tightening the Luer access device to stop blood from advancing along the catheter. Unfortunately, this procedure is also prone to user error, a lack of consistent and accurate control of blood flow through the system potentially leading to blood exposure and loss of body fluids, and unnecessary risk of contamination.

Thus, what are needed are improvements to many of the systems and methods described above. Such systems and methods can be improved by providing more efficient extravascular venting systems and methods.

BRIEF SUMMARY OF THE INVENTION

The present invention has been developed in response to problems and needs in the art that have not yet been fully resolved by currently available extravascular systems, devices, and methods. Thus, these systems, devices, and methods are developed to provide more efficient extravascular venting systems and methods.

A medical device may include a closed extravascular system having a fluid path and a gas vent in communication with the fluid path. The closed extravascular system may remain closed after gas vents from the fluid path through the gas vent. The gas vent may include a venting material and a user-activated rotation valve, a user-activated seal with a pull tab, at least two layers of fluid seal material separated by a layer of gas, a removable filter plug and a re-seal elastomer, and/or a cannula and a cartridge seal.

The gas vent may include a cannula with a first end and a second end, a venting material secured to the first end of the cannula, a push shaft with a first end and a second end, and a septum secured to the second end of the push shaft and in movable contact with the second end of the cannula. The gas vent may include a narrow vent hole and a floatable structure and/or a heavy structure in the fluid path and in communication with the narrow vent hole.

The gas vent may include a spring-loaded sealing member, a sealing member that expands when the sealing member comes into contact with liquid, a check valve, a moisture-cure material, and/or a porous membrane. The vent may be in direct communication with the fluid path.

The gas vent may include an expandable vent material, a cannula with a first end and a second end, and a septum in communication with the second end of the cannula. The first end of a cannula may be anchored within the expandable vent material. The vent material may be capable of expanding and drawing the second end of the cannula through the septum when the vent material is exposed to liquid.

A method of venting a medical device may include providing a closed extravascular system having a fluid path, providing a gas vent in communication with the fluid path, venting gas from the extravascular system through the gas vent, and maintaining a closed extravascular system during and after venting. The method may also include any of the following steps: closing the vent upon user-activation of the vent, saturating a first layer of venting material with liquid, removing the gas vent after venting, closing the vent with a floatable structure, closing the vent with a heavy structure, closing the vent with a spring-loaded sealing member, and/or closing the vent with an expandable sealing member. The step of providing a gas vent in communication with the fluid path may include providing the gas vent in direct communication with the fluid path. The method may further include curing a material to form a seal.

The gas vent may include an expandable vent material, a cannula with a first end and a second end, and a septum in communication with the second end of the cannula. This method may further include anchoring the first end of a cannula within the expandable vent material, expanding the vent material, and drawing the second end of the cannula through the septum as the vent material expands.

A medical device may include a means for providing access to the vascular system of a patient and a means for venting the means for providing access to the vascular system of a patient. The means for providing access to the vascular system of a patient may include a fluid path. The means for venting the means for providing access to the vascular system of a patient may communicate with the fluid path.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
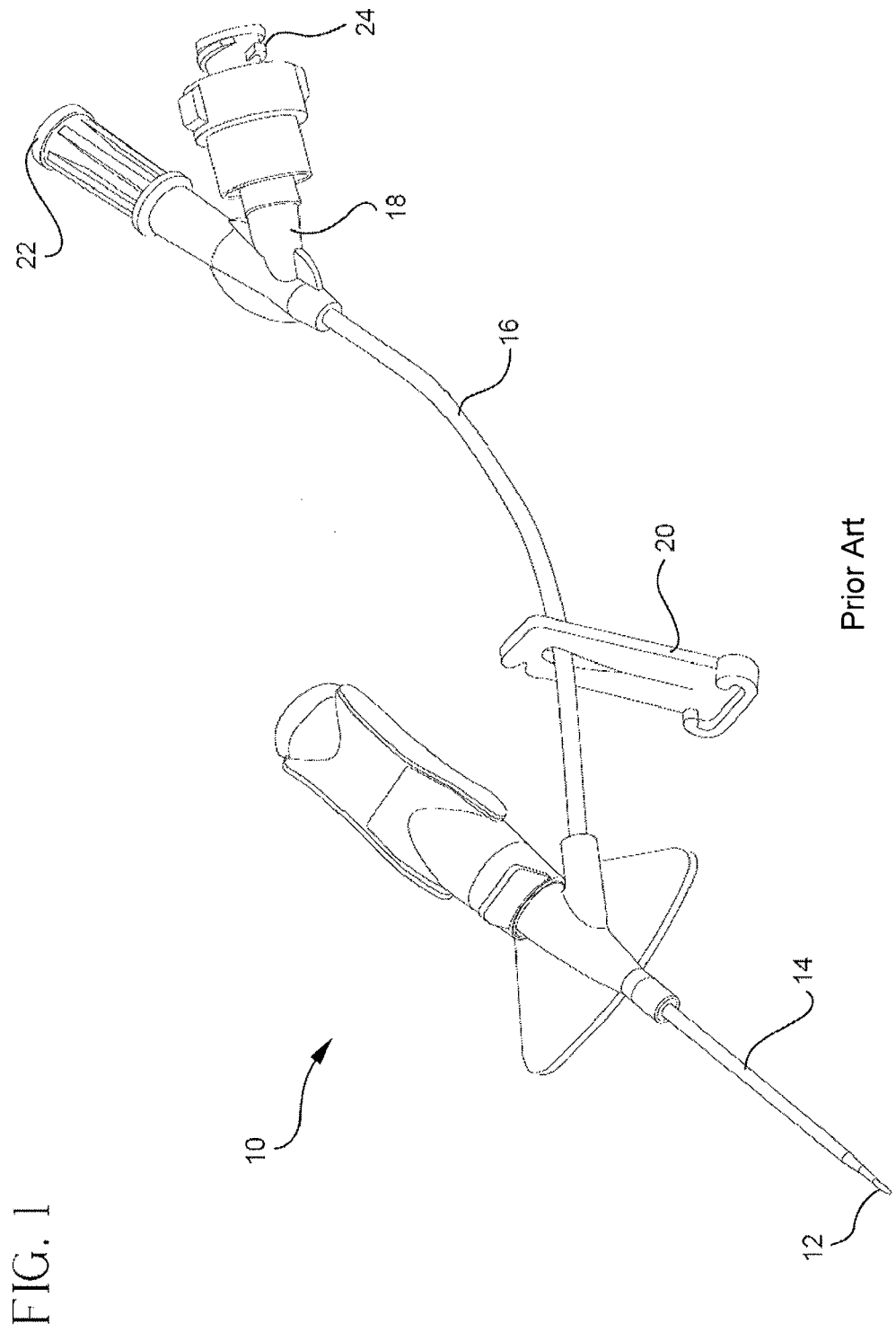
FIG. 1 is a perspective view of an extravascular system of vascular access devices.

Referring now to FIG. 1, an extravascular system 10, such as the BD NEXIVA™ Closed IV (intravenous) Catheter System, by Becton, Dickinson and Company, is used to communicate fluid with the vascular system of a patient. An example of the system 10, as shown in FIG. 1, includes multiple vascular access devices such as an intravascular needle 12; an over-the-needle, peripheral intravascular catheter 14 made from polyurethane; an integrated extension tubing 16 (also referred to herein as a catheter or an intravenous (IV) tube/tubing) with a Y adapter 18 and slide clamp 20; a vent plug 22; a Luer access device or port 24; and a passive needle-shielding mechanism 26. Any adapter used to connect two or more vascular access devices may be used in place of the Y adapter 18.

The system 10 is initially a closed system since it protects clinicians or operators from blood exposure during the catheter 14 insertion procedure. Since the needle 12 is withdrawn through a septum that seals after the needle 12 has been removed and both ports of the Y adapter 18 are closed, blood is contained within the system 10 during catheter 14 insertion. The pressure exerted on the needle 12 as it passes through the septum wipes blood from the needle 12, further reducing potential blood exposure. The slide clamp 20 on the integrated extension tubing 16 is provided to eliminate blood exposure when the vent plug 22 is replaced with another vascular access device such as an infusion set connection or another Luer access device or port 24.

As mentioned above, a current procedure of initiating the use of the extravascular system 10 is as follows. A device operator will insert the needle 12 into the vasculature of a patient and wait for flashback of blood to travel into the system 10 to confirm that the needle 12 is properly located within the vasculature of the patient. The blood travels into and along the catheter 14 and extension tubing 16 because a vent plug 22 permits air to escape the system 10 as blood enters the system 10. After an operator confirms proper placement, and after adequate venting of the system 10 has occurred, the operator clamps the catheter 16 to halt the progression of blood through the catheters 14 and 16, removes the vent plug 22 (temporarily opening the otherwise closed extravascular system 10), replaces the vent plug 22 with another vascular access device such as an infusion set connection or a Luer access device similar or identical to Luer access device or port 24 (re-closing the extravascular system 10), unclamps the catheter 16, flushes the blood from the catheters 14 and 16 back into the vasculature of the patient, and re-clamps the catheter 16.

Alternate vents and venting procedures are desired and will be discussed with reference to the figures following FIG. 1. Specifically, vents and venting procedures that, among other advantages, do not require opening of an otherwise closed extravascular system may be desired.

Vents described throughout this disclosure may be placed anywhere on or in an extravascular system. For example, a vent may be placed near the terminus of a fluid path of an extravascular system in order to ensure that all gas within the entire fluid path of the extravascular system is vented from the extravascular system. As another example, a vent may be placed at or near the start of the fluid path, just outside the vascular system of a patient, in order to vent the extravascular system while minimizing the flow of blood from the vascular system into the extravascular system as a result of venting. As another example, the vent may be placed at any point in between the start or end of the fluid path of the extravascular system, such as on a port or on the intravenous tube. For example, where a vent is placed in the middle of an extravascular system, the vent will vent gas as fluid is pulled through the system in either direction. Vents that remain permeable to gas in the presence of a liquid are preferred in this embodiment. Vents may be placed in the middle of the extravascular system in order to avoid creating areas of stagnant and/or otherwise trapped blood and air bubbles that would otherwise result from the presence of a vent at an end of the extravascular system.

Vents may also be placed in areas of stagnant flow within the extravascular system in order to remove all gas and/or stagnant fluid from the venting area. One or more vents, and one or more of the elements or features thereof, may be combined in any combination and applied to an extravascular system. Such combination may occur in order to eliminate stagnant gas and liquid, minimize and/or maximize blood reflux, ensure full venting of gas from the extravascular system, and achieve other desired benefits.

Figure 2A:
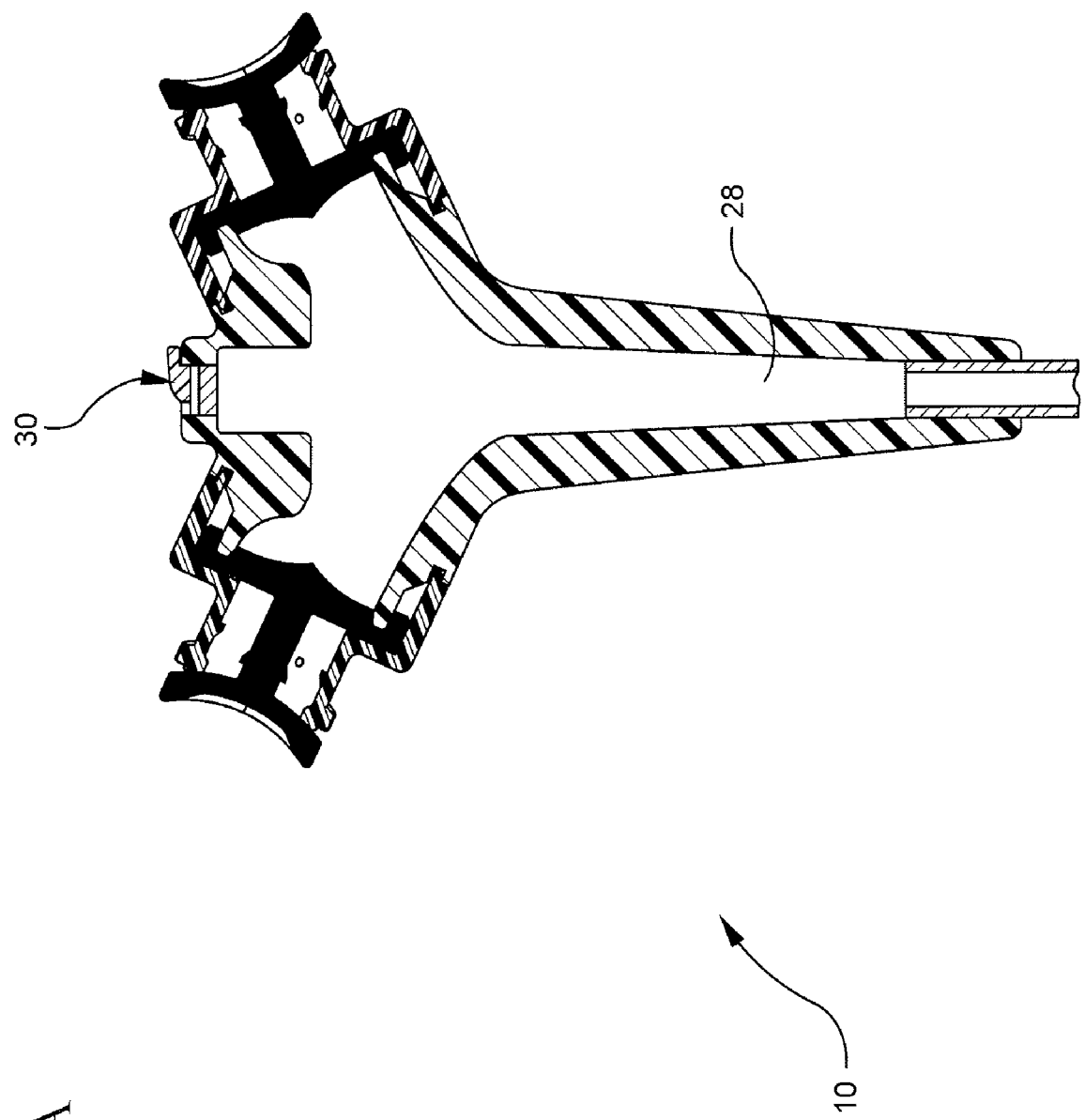
FIG. 2a is a cross section view of an extravascular system with multiple vent embodiments.

Referring now to FIG. 2a, an extravascular system 10 includes a fluid path 28 within the interior of the extravascular system 10. The fluid path 28 is in communication with a vent 30, and the vent 30 is capable of venting gas from the fluid path 28 of the system 10. The extravascular system 10 remains closed both during and after venting of gas through the vent 30. In other words, an operator of the extravascular system 10 may vent the system 10 without ever removing the vent 30 from the system 10 in a manner that exposes the operator to the fluid path 28 of the system 10.

The vent 30 may include multiple embodiments. In one embodiment illustrated in FIG. 2b, the vent 30 includes a venting material 32 and a user-activated rotation valve 34. An operator or user may rotate the rotation valve 34 in order to close exposure to the vent plug or venting material 32. Airflow or gas flow will travel from the fluid path 28, through the venting material 32, and out the user-activated rotation valve 34 when the valve 34 is open. When the valve 34 is closed, no air or other fluid will travel through the vent 30.

Figure 2C:
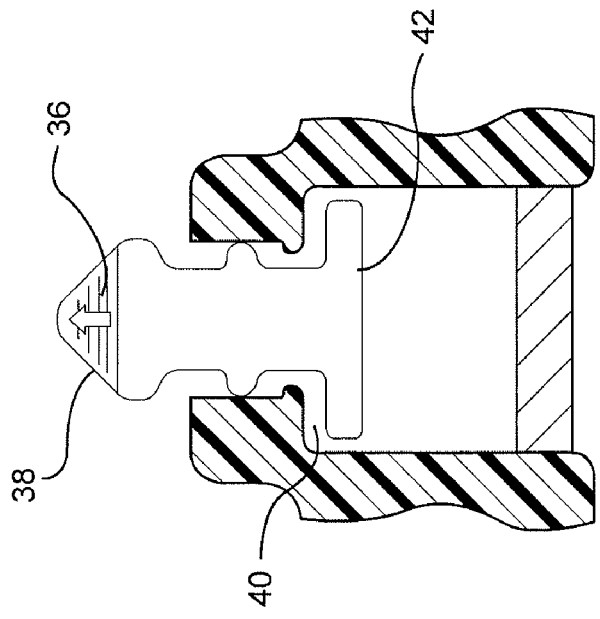
FIG. 2c is a cross section view of another embodiment of the vent illustrated in FIG. 2.
Figure 2B:
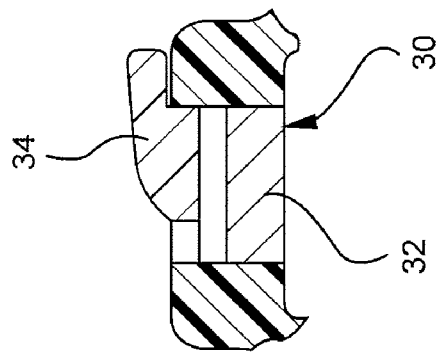
FIG. 2b is a cross section view of one embodiment of the vent illustrated in FIG. 2.

In another embodiment illustrated in FIG. 2c of the vent 30, the vent 30 includes a user-activated seal 36 with a pull tab 38. Air or other gas will travel around the edges 40 of the user-activated seal 36 until a user pulls upward on the pull tab 38, causing a bottom disc 42 of the seal 36 to come into contact with an inner surface of the body of the extravascular system 10. When the disc 42 comes into contact with the surface of the extravascular system 10, the user-activated seal 36 will close the airflow channels adjacent the seal 36, preventing any further gas or other fluid from escaping the fluid path through the vent 30 into the external environment in which the system 10 is placed.

Figure 2D:
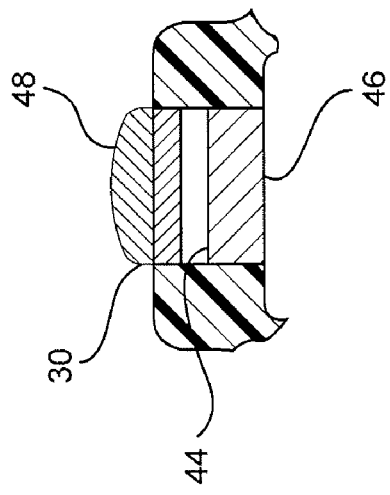
FIG. 2d is a cross section view of another embodiment of the vent illustrated in FIG. 2.

In another embodiment of the vent 30 illustrated in FIG. 2d, the gas vent 30 includes at least two layers of fluid seal or other venting material separated by a layer of gas 44. A first layer of fluid seal material 46 is exposed to the inner surface of the system 10 that is in contact with the fluid path 28. A second layer of fluid seal material 48 is separated from the first seal 46 by the layer of gas 44 and is exposed to the external environment in which the extravascular system 10 is placed. In use, an operator will allow the system 10 to vent through the vent 30, causing air to escape through both layers 46 and 48 into the external environment. After all or a substantial portion of gas has escaped the fluid path 28, blood or other liquid will come into contact with the first layer 46. As blood or other liquid comes into contact with the first layer 46, the liquid will seep or weep through the first layer 46, saturating the first layer 46 of venting material. Because the second layer 48 is separated from the first layer 46 by a layer of gas 44, the liquid that has saturated the first layer 46 will not travel to the second layer 48. Since liquid will not travel to the second layer 48, an operator will never be exposed to blood from a patient during the venting procedure for the extravascular system 10.

Figure 3:
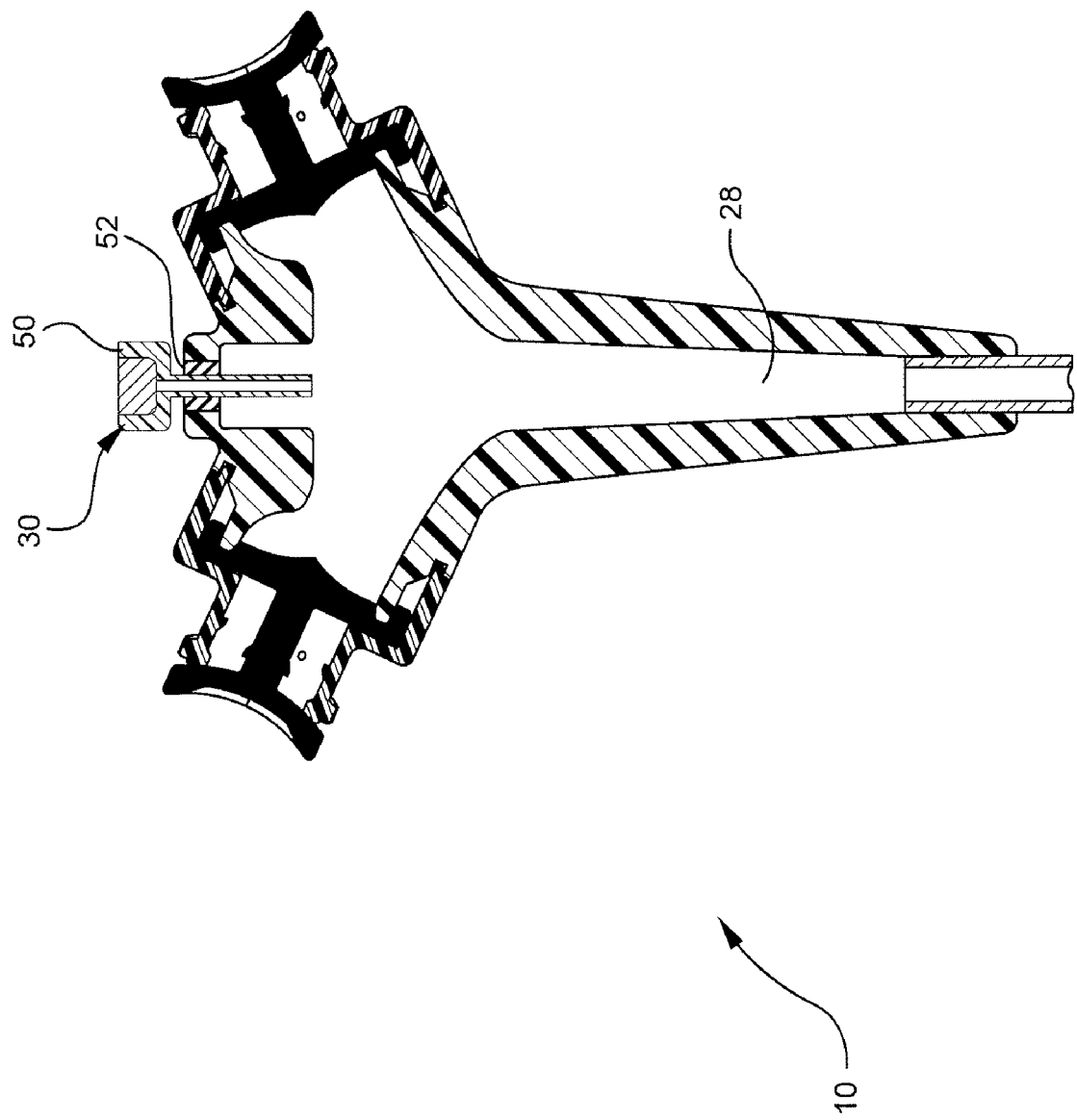
FIG. 3 is a cross section view of multiple embodiments of an extravascular system with a removable filter plug and a re-seal elastomer.

Referring now to FIG. 3, an extravascular system 10 includes a fluid path 28 in communication with a vent 30. The vent 30 includes a removable filter plug 50 and a re-seal elastomer 52. The vent 30 is placed at or near vascular access devices on the system 10 capable of providing fluid access to the system 10. The vent 30 may be placed at or near the terminus of the system 10 in order to allow fluid, including gas, blood, saline, and water, to fill the internal chamber of the fluid path directly adjacent any vascular access devices of the system 10. Providing this location of the vent 30 on the system 10 will provide less gas and other stagnant fluid entrapment at this location.

The vent 30 may be placed on an extravascular system with a Y or other port. The removable filter plug 50 may be removed from the system 10 after the system 10 is fully vented of gas and has been self-primed by allowing liquid to travel up to the vent 30 and neighboring vascular access devices. After the removable filter plug 50 is removed from the system 10 the re-seal elastomer 52 will seal the system 10, preventing any further unwanted fluid from exiting the fluid path 28 into the external environment in which the system 10 is placed.

Figure 4:
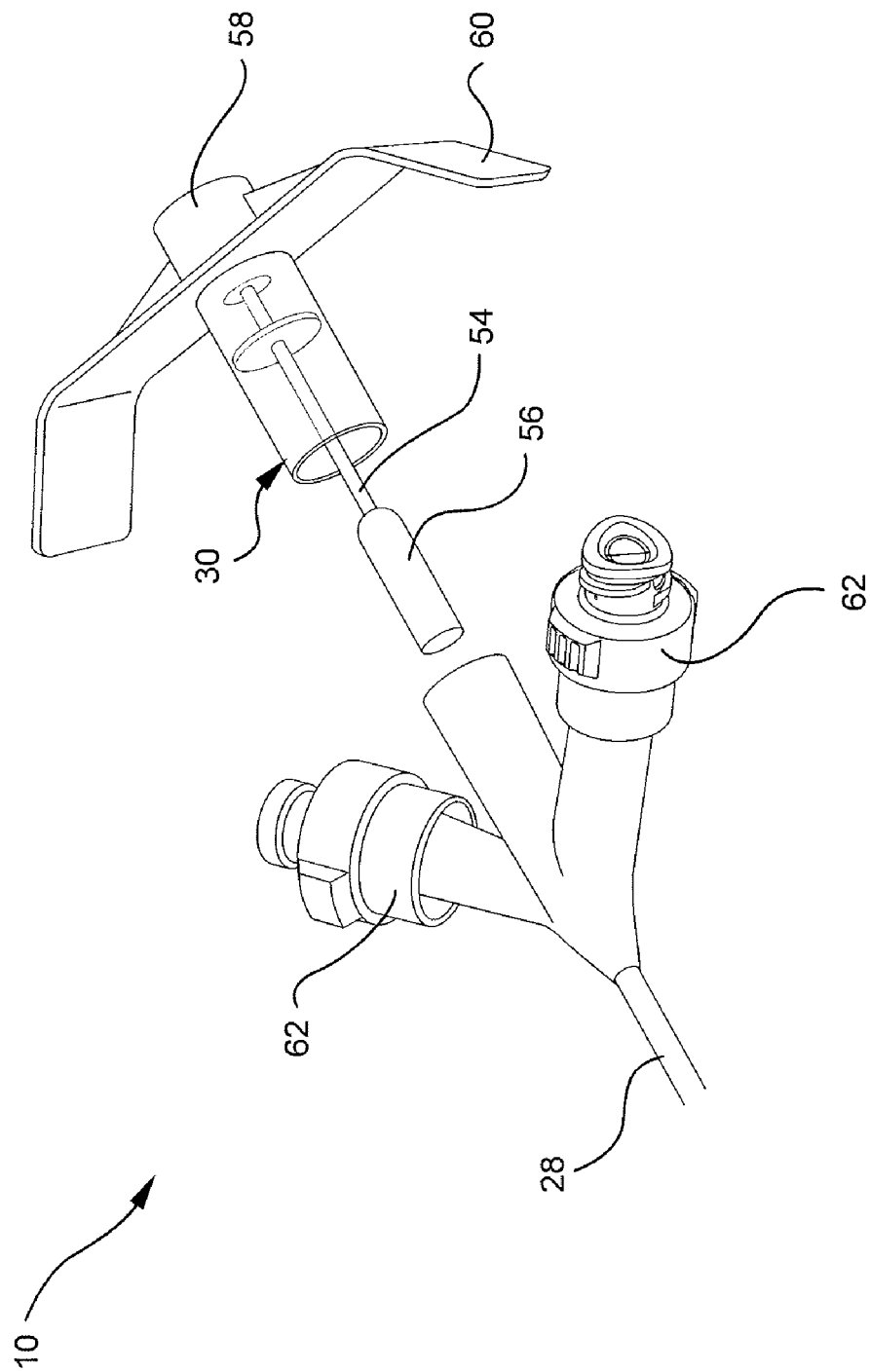
FIG. 4 is a perspective view of an extravascular system and a vent having a cannula and a cartridge seal.

Referring now to FIG. 4, an extravascular system 10 includes a fluid path 28 in communication with a vent 30. The vent 30 includes a cannula 54 and a cartridge seal 56. The cannula 54 provides a gas permeable vent through which gas may travel from the fluid path 28, through the cannula 54, across a venting material 58, and into the external environment in which the system 10 is placed. After the cannula 54 and venting material 58 are removed from the system 10, the cartridge seal 56 will seal the lumen in which the cannula 54 resided, preventing any further escape of gas and other fluid from the fluid path 28 into the external environment. The vent 30 may also include additional protective structure 60, which may or may not include antimicrobial coatings or other treatments on its surface, to protect the surfaces of vascular access devices 62 at our neighboring event.

Figure 5:
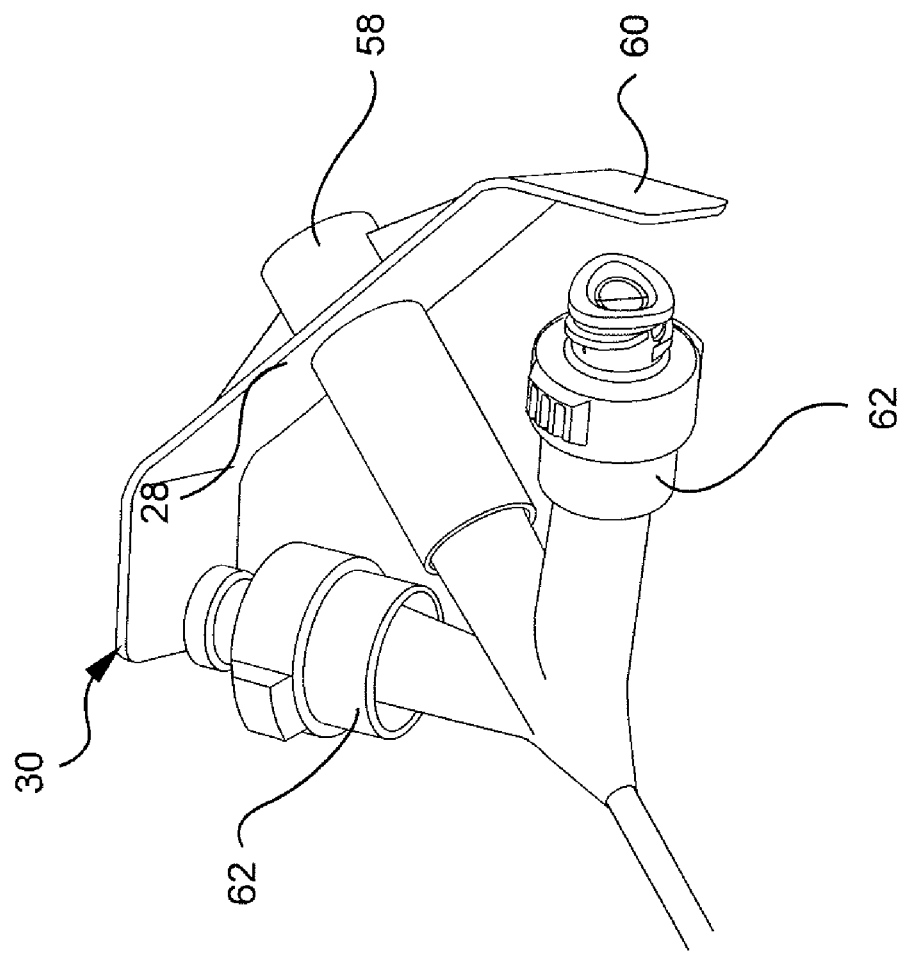
FIG. 5 is another perspective view of the extravascular system and vent of FIG. 4.
Figure 5:
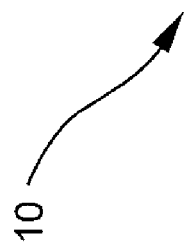

Referring now to FIG. 5, another perspective view of the extravascular system 10 of FIG. 4 is shown.

Figure 6:
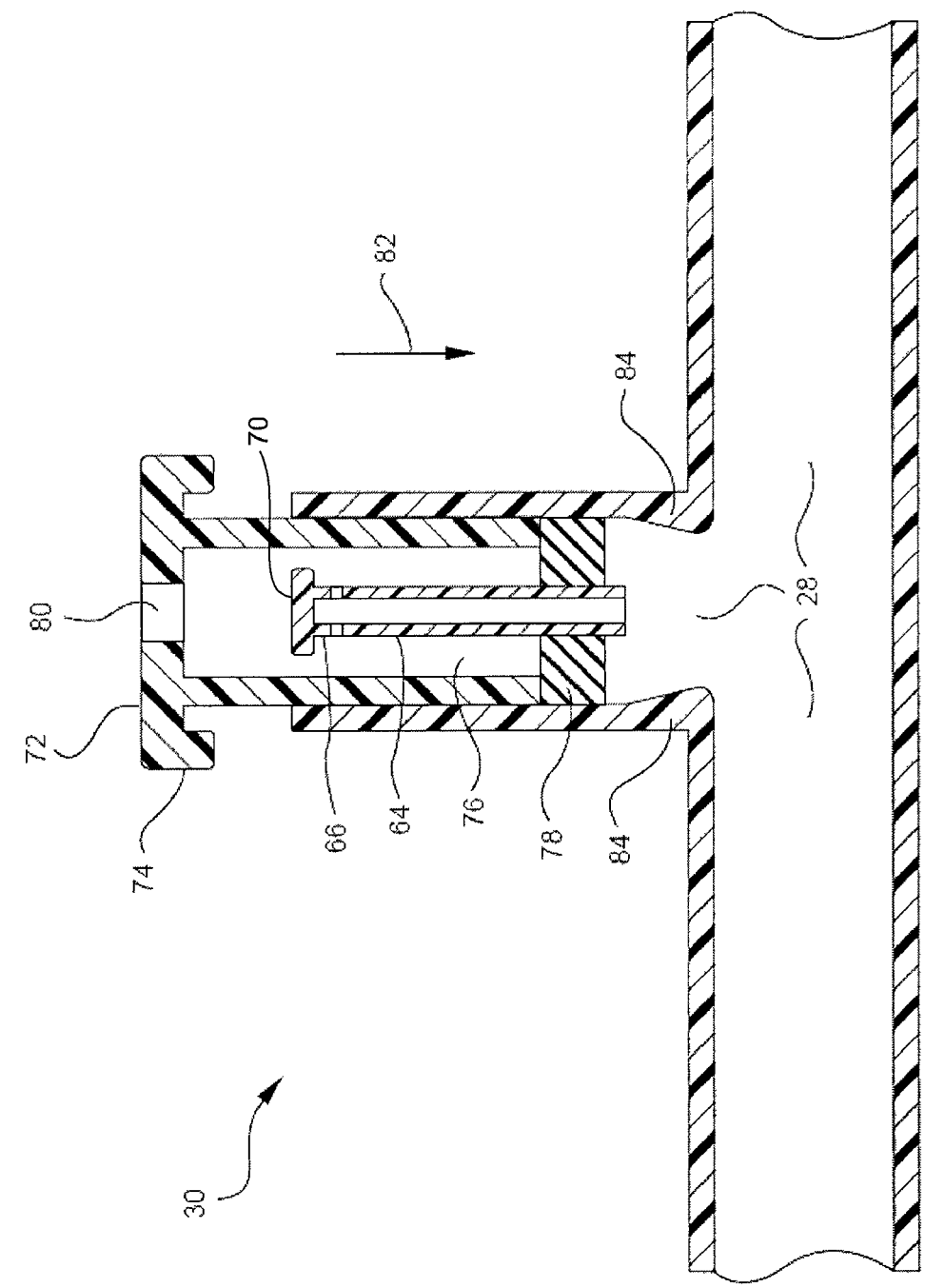
FIG. 6 is a cross section view of an extravascular system and a vent with a push shaft.

Referring now to FIG. 6, an extravascular system 10 includes a fluid path 28 in communication with a vent 30. The gas vent 30 includes a cannula 64 with a first end 66 and a second end 68, a venting material 70 secured to the first end 66 of the cannula 64, a push shaft 72 with a first end 74 and a second end 76, and a septum 78 secured to the second end 76 of the push shaft 72 and in movable contact with the second end 68 of the cannula 64. The septum 78 is in contact with the outer surface of the cannula 64 near the second end 68. The second end 68 of the cannula 64 is exposed to the fluid path 28 of the system 10.

During venting of the system 10, gas will flow from the fluid path 28 into the second end 68 of the cannula 64, through the first end 66 and the venting material 70, out a hole 80 in the first end 74 of the push shaft 72, and into the external environment in which the system 10 is placed. After adequate venting, an operator may close the vent 30 by pushing the first end 74 of the push shaft 72 in a direction 82. As the push shaft 72 advances in a direction 82, the second end 76 of the push shaft 72 will force the septum 78 beyond the second end 68 of the cannula 64. As the septum 78 advances beyond the second end 68, the septum will be compressed by tapered walls 84 located on the interior surface of the extravascular system 10. Under compression of the tapered walls 84, the septum 78 will close the lumen that existed within the septum 78 when the second end 68 penetrated the septum 78. As the septum lumen 78 closes, the vent 30 will be sealed from further gas or other fluid escaping the system 10 into the external environment.

Figure 7:
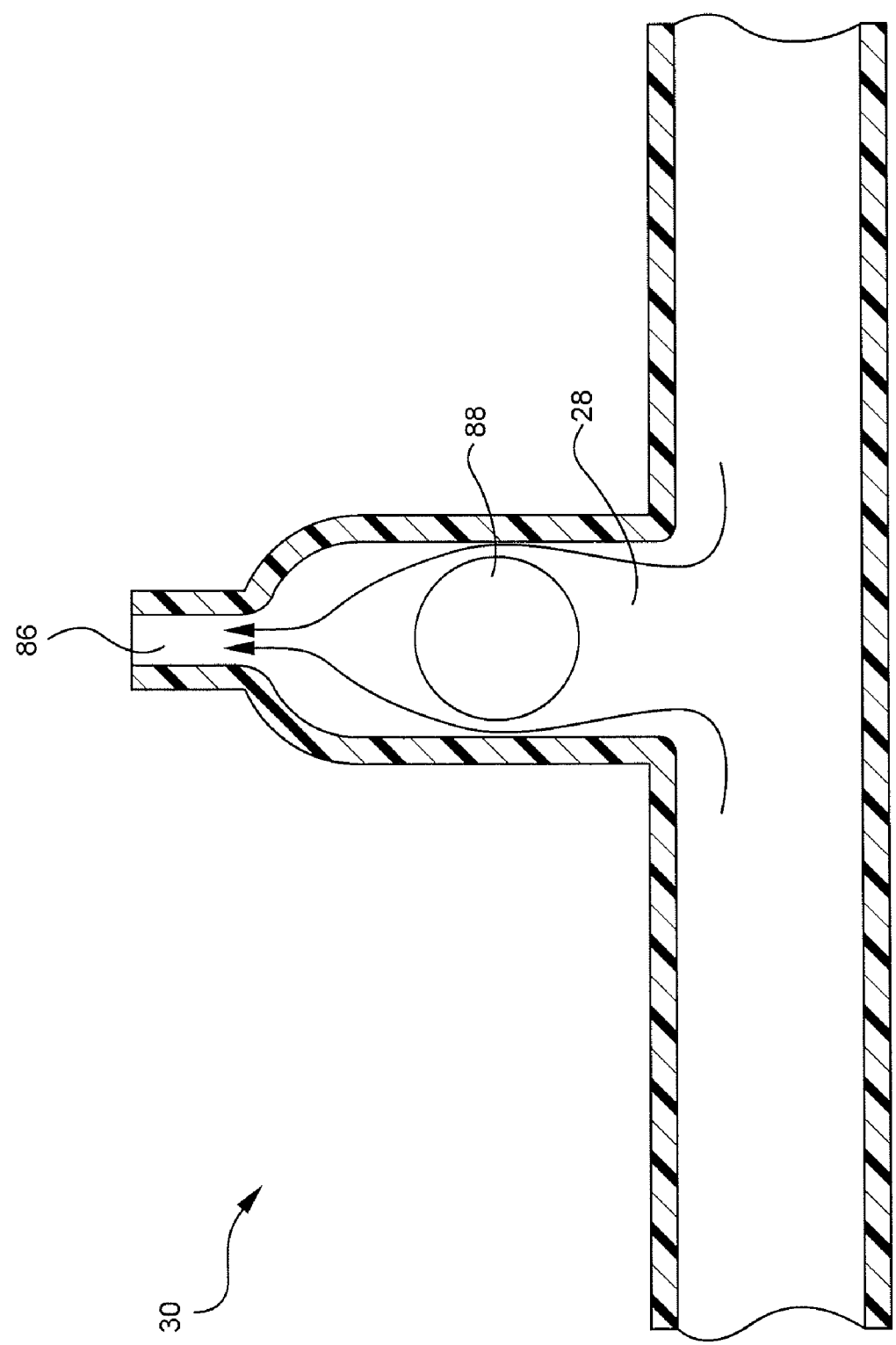
FIG. 7 is a cross section view of an extravascular system with a vent hole and a floatable structure.

Referring now to FIG. 7, an extravascular system 10 includes a vent 30 having a narrow vent hole 86 and a floatable structure 88. The floatable structure 88 resides within the fluid path 28 of the system 10 and is in communication with the narrow vent hole 86.

The floatable structure 88 is preferably not permeable to gas or other fluid. The floatable structure 88 is small enough to permit air or other gas to flow past the floatable structure 88, through the remainder of the fluid path 28, through the narrow vent hole 86, and into the external environment in which the system 10 is placed. The floatable structure 88 is capable of sealing the narrow vent hole 86 when in contact therewith. The floatable structure 88 may be formed of a material that expands when it comes into contact with liquid.

Figure 8:
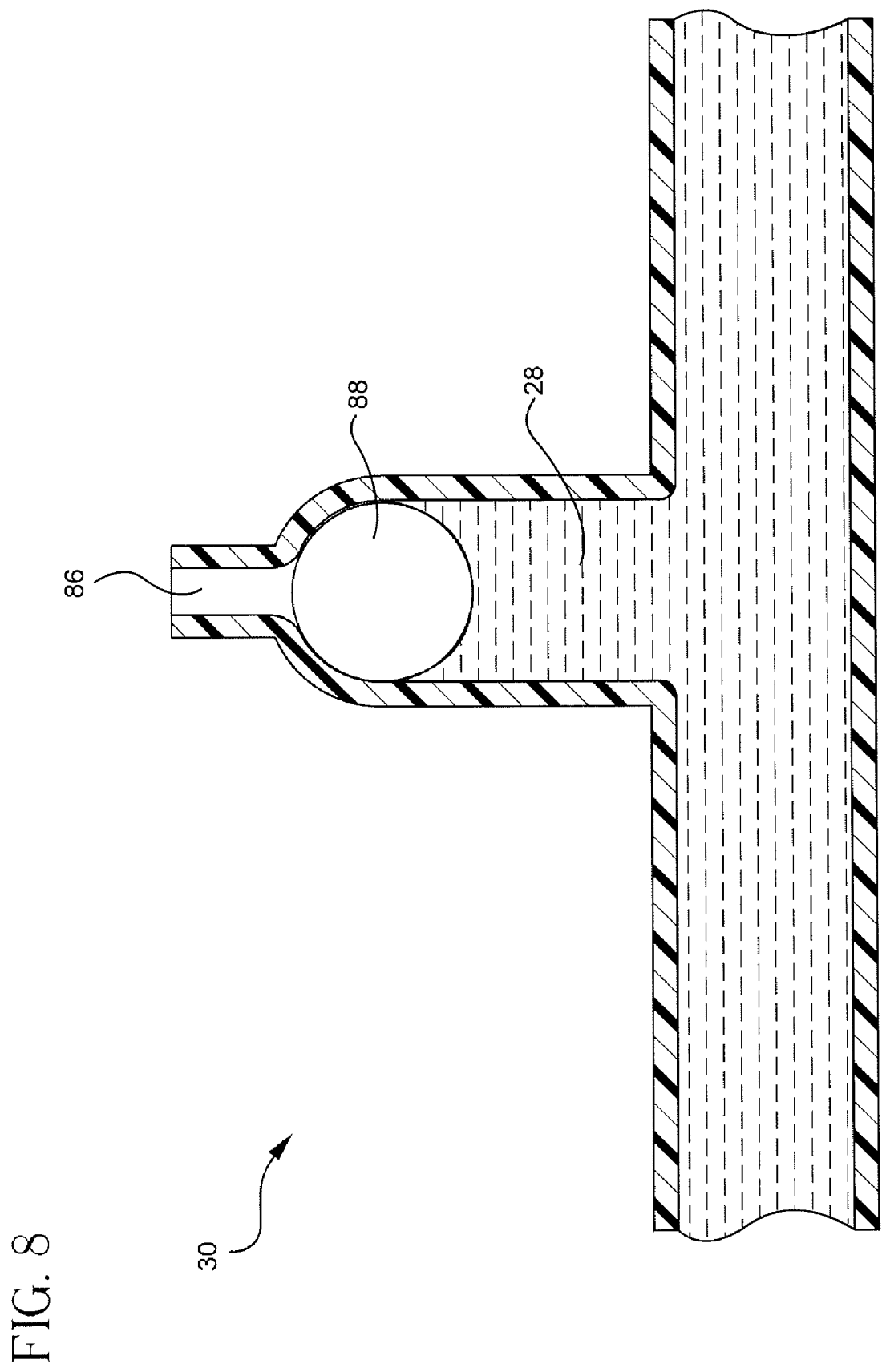
FIG. 8 is a cross section view of the extravascular system of FIG. 7 with the floatable structure sealed to the narrow vent hole.

Referring now to FIG. 8, the vent 30 of FIG. 7 is shown with liquid in the fluid path 28. With liquid placed in the fluid path 28, the floatable structure 88 has been forced upward as a result of its buoyancy on top of the liquid into the narrow vent hole 86, causing the narrow vent hole 86 to become sealed to any further flow of gas or other liquid. The material of the floatable structure 88 may expand as a result of its contact with liquid, causing the floatable structure 88 to fill and seal both the narrow vent hole 86 and the neighboring upper portion of the fluid path 28, in order to provide a long term seal against any future flow of gas or other fluid. The embodiment described with reference to FIGS. 7 and 8 is subject to certain limits, in that the vent 30 must be placed upright in order for the floatable structure to float in the direction of the narrow vent hole 86. Thus, an alternate embodiment, as described with reference to FIG. 9, may be preferred.

Figure 9:
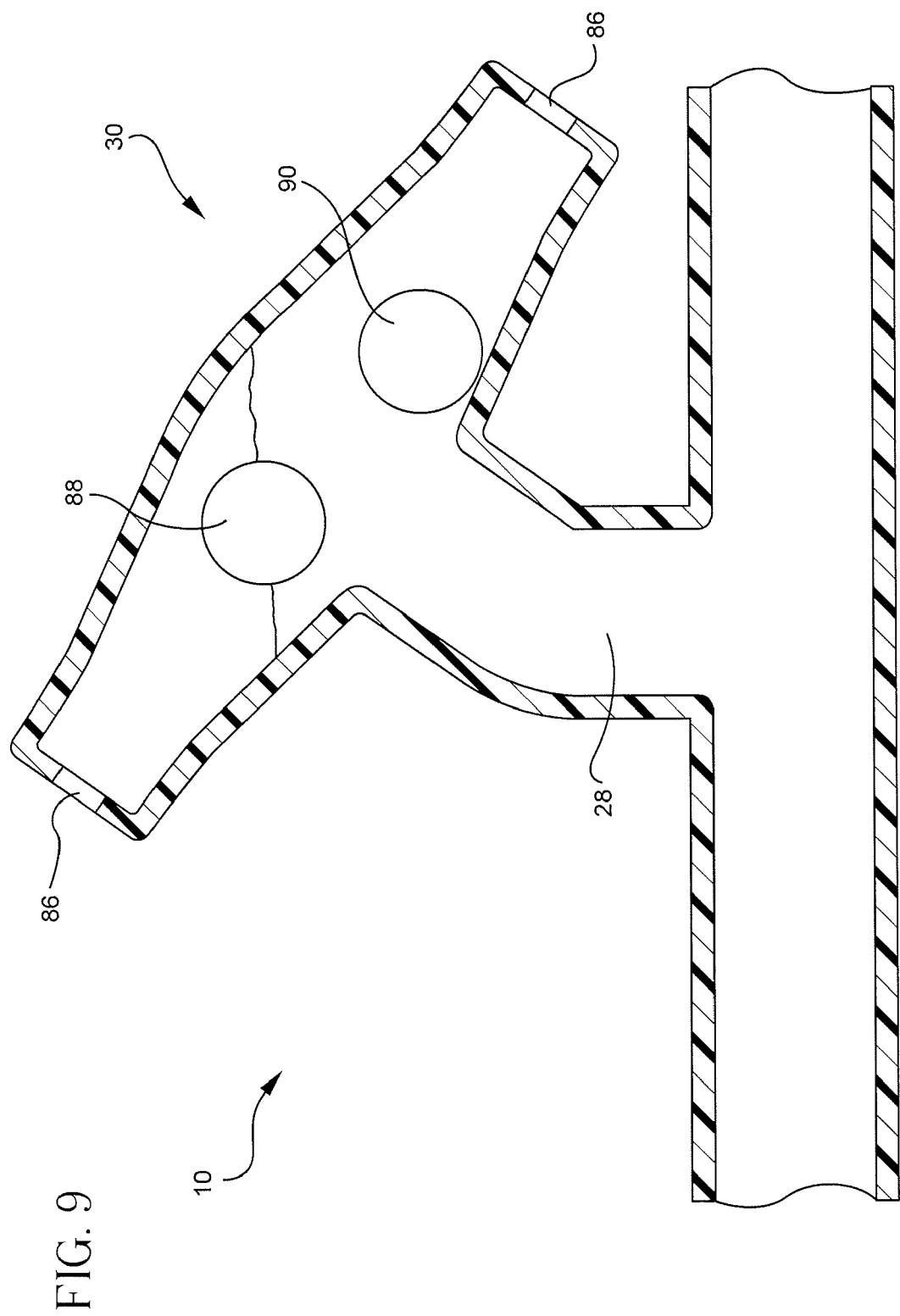
FIG. 9 is a cross section view of an extravascular system with at least one narrow vent hole, a floatable structure, and a heavy structure.

Referring now to FIG. 9, an extravascular system 10 includes a fluid path 28 and a vent 30 in communication with the fluid path 28. The vent 30 may include at least one narrow vent hole 86 and one or more sealing structures, such as a floatable structure 88 and/or a heavy structure 90. The heavy structure 90 is capable of sinking in the presence of a liquid. Both the floatable structure 88 and the heavy structure 90 are placed within the fluid path 28 and are in sealing communication with the at least one narrow vent hole 86.

The floatable and heavy structures 88 and 90 permit gas to travel around the structures 88 and 90 and through the at least one narrow vent hole 86 to the external environment. However, after liquid enters the fluid path 28, the liquid will cause the floatable structure 88 to rise towards an upper narrow vent hole 86 and will simultaneously cause the heavy structure 90 to sink towards a lower narrow vent hole 86. In this manner, either an upper or a lower vent hole 86 may be sealed by a sealing structure in response to the presence of a liquid within the fluid path 28. As with the embodiment described with reference to FIGS. 7 and 8, the embodiment described with reference to FIG. 9 may include an expandable material used as either of these structures 88 and 90 in order to provide a long term or more effective seal of the fluid path 28 and/or the at least one narrow vent hole 86.

Figure 10:
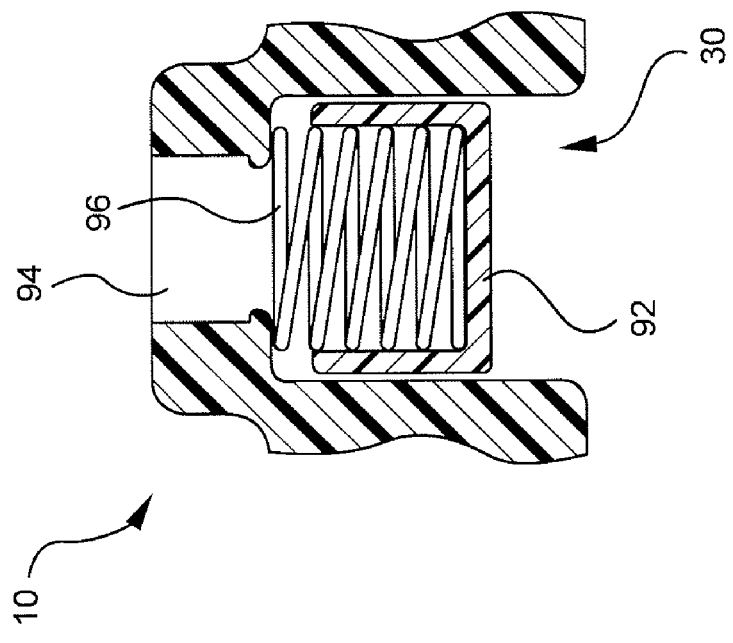
FIG. 10 is a cross section view of an extravascular system and a vent including a spring-loaded sealing member

Referring now to FIG. 10, an extravascular system 10 includes a fluid path 28 in communication with a vent 30. The vent 30 includes a spring-loaded sealing member 92 secured to the walls of the system 10 adjacent a vent hole 94 by means of a light spring 96. The light spring 96 requires very little force in order to become compressed. Thus, the spring-loaded sealing member 92 will allow gas to travel around the sealing member and through the vent hole 94, escaping to the external environment, while the light spring 96 is uncompressed.

Figure 11:
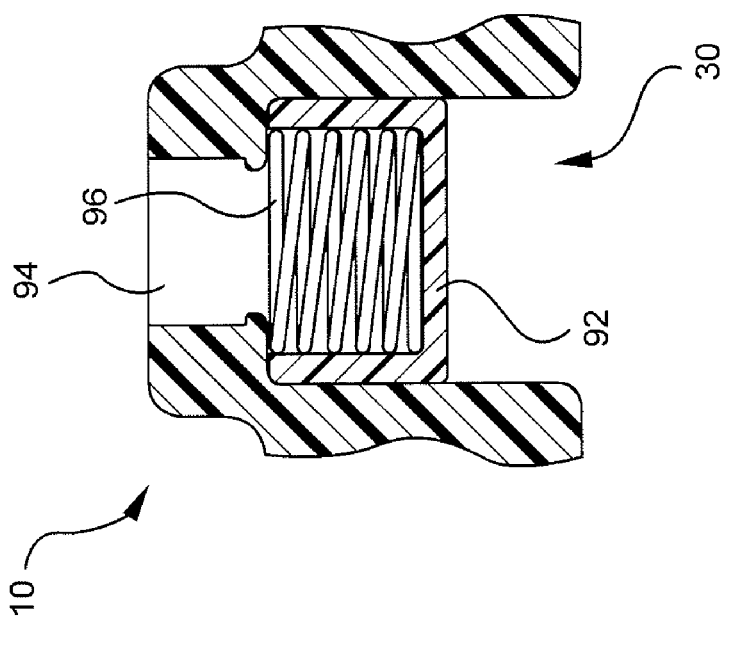
FIG. 11 is a cross section view of the extravascular system of FIG. 10 with the spring-loaded sealing member activated.

Referring now to FIG. 11, the vent 30 described with reference to FIG. 10 is shown. Liquid has entered into the fluid path 28 of the system 10, providing force against the spring-loaded sealing member 92. The force against the spring-loaded member 92 in turn has caused the light spring 96 to become compressed. Since the spring 96 is compressed, the spring-loaded sealing member 92 is now in contact with the wall of the system 10 such that no gas or other fluid, such as liquid, may escape the system 10 through the vent hole 94 and into the external environment. In an alternate embodiment, any expandable material capable of expanding upon coming into contact with a liquid, may be employed as a vent 30 structure with a spring 96 in order to provide a vent capable of sealing upon liquid contact. In this embodiment, after liquid provides force against the spring, any portion of the expandable material may be transferred into the lumen of the vent hole 94 as the material expands to seal off the vent hole 94.

Figure 12:
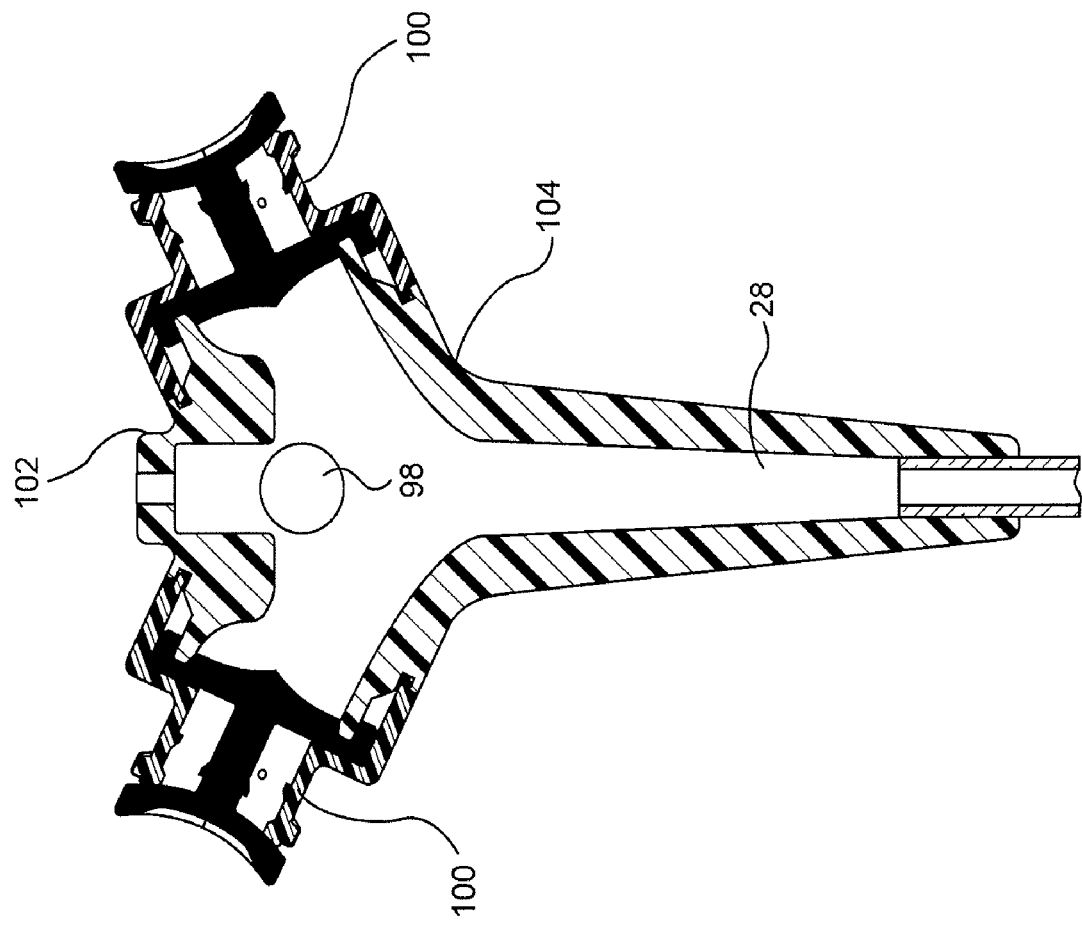
FIG. 12 is a cross section view of multiple embodiments of an extravascular system with a check valve gas vent.

Referring now to FIG. 12, an extravascular system 10 includes a fluid path 28 in communication with a vent 30. The vent 30 includes a check valve 98. The check valve 98 may be a ball check or a plug check capable of sealing a gas path in communication with the fluid path 28. The vent 30 may be placed in proximity with other vascular access devices, such as Luer access devices, on a Y-shaped adapter of an extravascular system 10.

The ball or plug check valve 98 is located in a position between two neighboring vascular access devices 100 to allow gas to escape the system 10 during venting. When liquid hits the ball or plug valve 98, the ball or plug moves into a neck 102, sealing off the vent 30 from any further gas or other fluid transfer between the fluid path 28 and the external environment.

Injection of a liquid from either of the neighboring vascular access devices 100 would also press or force the ball or plug of the check valve 98 further into the neck 102 in order to seal the vent 30. The surface of the ball or plug of the check valve 98 may be such that after entry into the neck 102, the ball or plug is reluctant to exit the neck 102 and re-enter the fluid path 28. In addition, the ball or plug of the check valve 98 may include or be formed of any expandable material capable of expanding in the presence of a liquid. Thus the ball or plug could expand, after being forced by a liquid into the neck 102, causing the check valve 98 to fully and permanently seal the vent 30. The unique location of the vent 30 between the two neighboring vascular access devices 100 on a Y-shaped connector of the extravascular system 10 may minimize air, gas or other stagnant fluid volume within the Y-shaped adapter 104. Alternately, a T-shaped adapter may employ the vent 30 between two neighboring vascular access devices 100.

The embodiments described with reference to FIG. 12 may advantageously provide a vent that is in direct communication with the active fluid path 28 of the system 10. In other words, no unnecessary volume is added to the vent in order to extend the vent away from the fluid path shared by neighboring vascular access devices 100. Rather, the vent 30 is located directly within the fluid path 28 between the downstream fluid path of the system 10 and the upstream fluid path of each particular neighboring vascular access device 100. This location prevents any dead gas or fluid volume within the fluid path 28 adjacent the vent 30.

Figure 13:
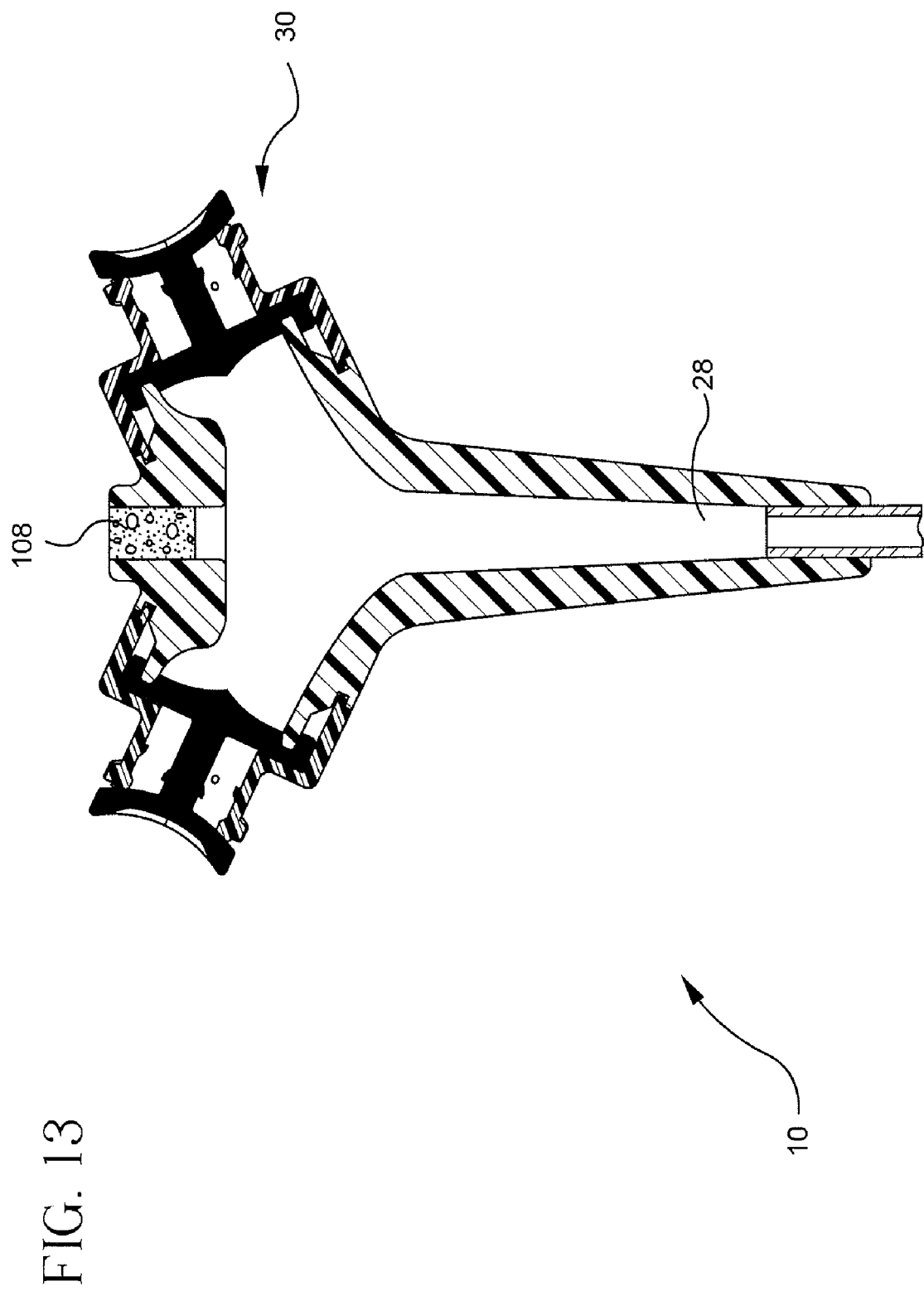
FIG. 13 is a cross section view of an extravascular system with a moisture-cure material.

Referring now to FIG. 13, an extravascular system 10 includes a fluid path 28 and a vent 30 in communication with the fluid path 28. The vent 30 includes a moisture-cure material 108 that is permeable to gas in the absence of a liquid.

Figure 14:
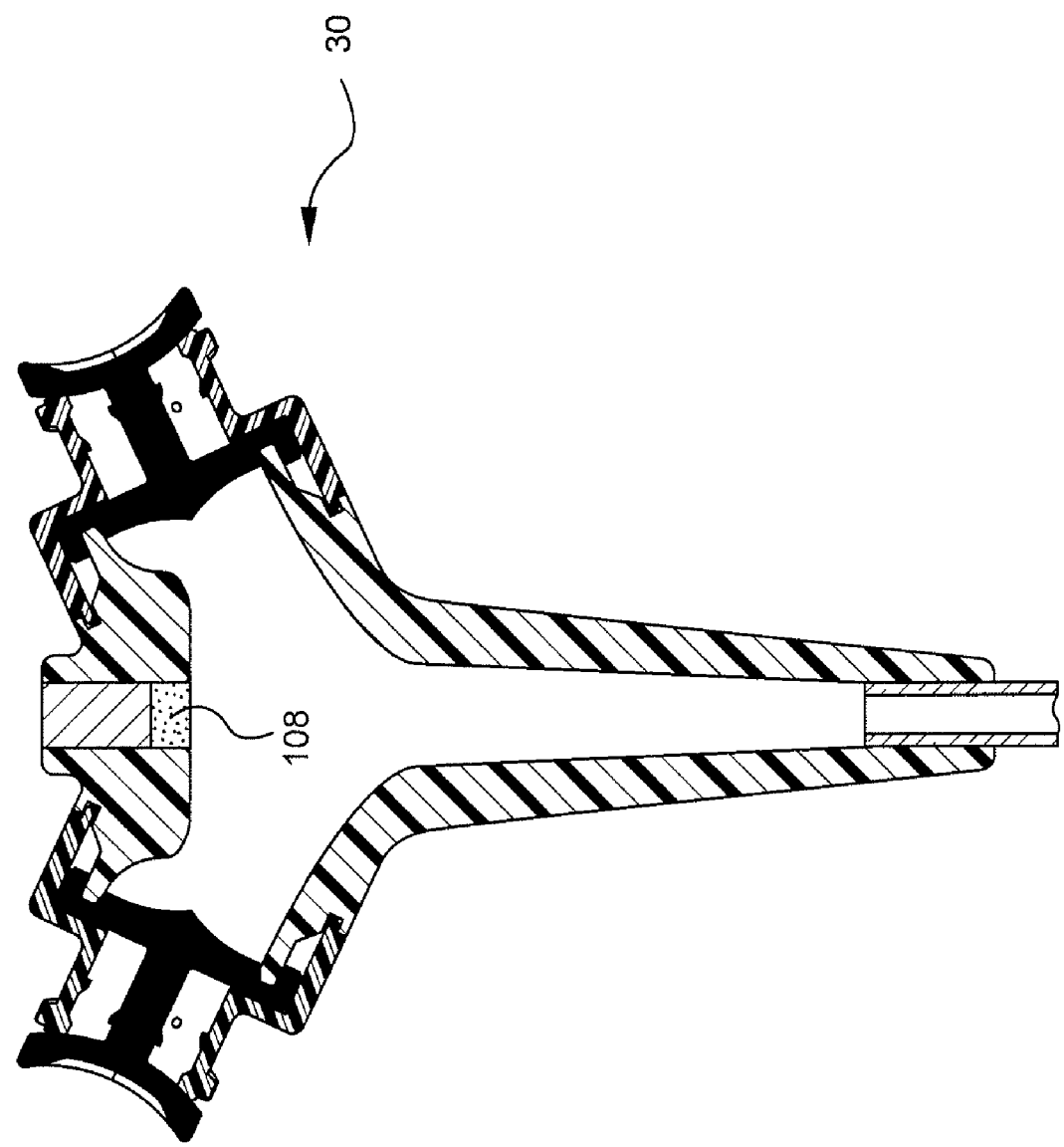
FIG. 14 is a cross section view of the extravascular system of FIG. 13 with the moisture-cure material cured.

Referring now to FIG. 14, the vent 30 of FIG. 13 is shown after liquid has entered into the fluid path 28 of the system 10. The liquid, such as water or blood, has caused the moisture-cure material 108 to become cured. After curing, the moisture-cure material 108 is no longer permeable to any fluid, including gas and liquid. Thus, the moisture-cure material 108 of the vent 30 described with reference to FIGS. 13 and 14 provides a vent capable of venting gas from the system 10 without permitting the escape of liquid after the liquid has come into contact with the material 108.

Figure 15:
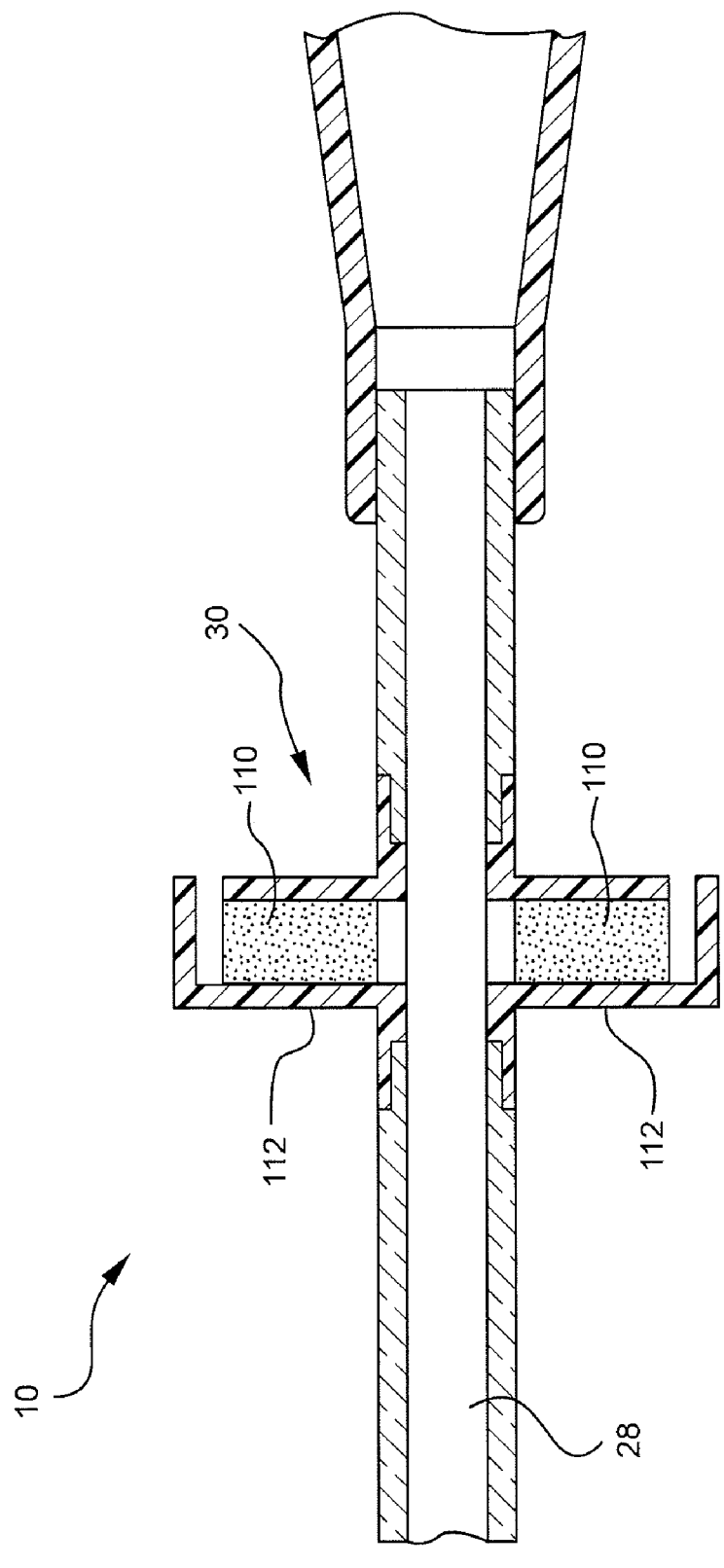
FIG. 15 is a cross section view of an extravascular system with a porous membrane vent.

Referring now to FIG. 15, an extravascular system 10 includes a fluid path 28 in communication with a vent 30. The vent 30 includes a porous membrane 110 secured by a housing 112 within the body of the system 10. The membrane 110 is gas, but not liquid, permeable. Thus, the vent 30 permits gas to escape from the fluid path 28 until the fluid path 28 includes only liquid.

Figure 16:
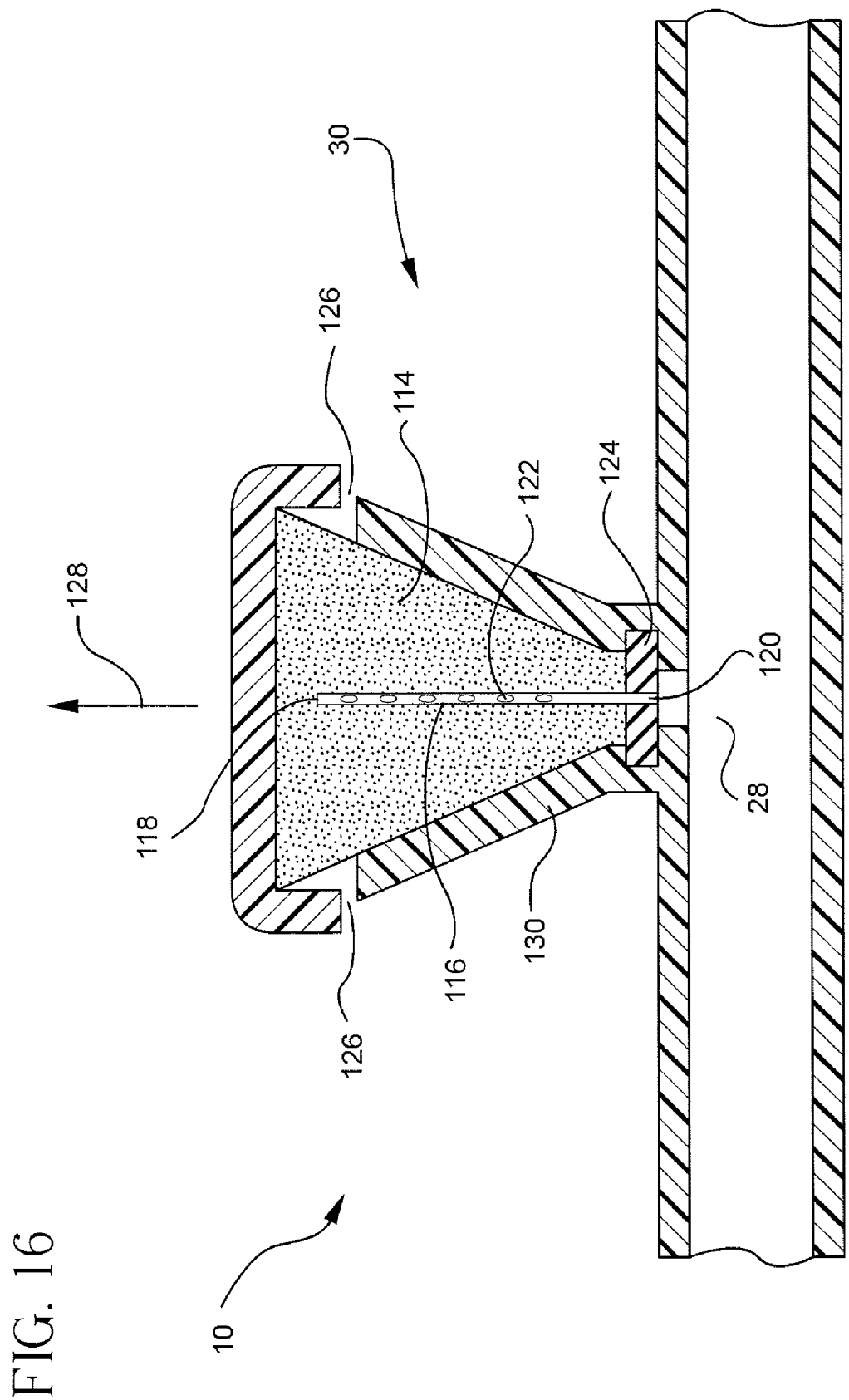
FIG. 16 is a cross section view of an extravascular system with a vent having an expandable vent material, a cannula, and a septum.

Referring now to FIG. 16, an extravascular system 10 includes a fluid path 28 in communication with a vent 30. The vent 30 includes an expandable vent material 114 that is hydrophilic. The vent 30 also includes a cannula 116 with a first end 118 and a second end 120. The cannula may include multiple pores 122 along its length and in communication with the expanding material 114. The vent 30 also includes a septum 124 in communication with the second end 120 of the cannula 116. The first end 118 of the cannula 116 is anchored within the expandable vent material 114. The expandable vent material 114 is capable of expanding and drawing the second end 120 of the cannula 116 through the septum 124 when the vent material 114 is exposed to liquid from the fluid path 28.

During venting, gas will travel from the fluid path 28 through the second end 120 of the cannula 116, through the pores 122 and first end 118 of the cannula 116, through the expanding material 114, through vent holes 126, and into the external environment in which the system 10 is placed. After all or substantially all gas has exited the system 10 through the vent 30, liquid from the fluid path 28 will travel through the second end 120 of the cannula 116, through the pores 122 and end 118 of the cannula 116, and into the venting material 114. As liquid travels into the venting material 114, the venting material 114 will expand, causing the venting material to travel in a direction 128 within a wedged body 130 of the vent 30. As the expanding material 114 travels in a direction 128, the expanding material 114 will draw the anchored first end 118 of the cannula 116 in the direction 128. Since the septum 124 is secured to the body of the system 10, as the cannula 116 travels in a direction 128, the second end 120 of the cannula 116 will exit the septum 124. After the cannula 116 has fully exited the septum 124, the septum 124 will self-seal under compression, causing the lumen that previously existed in the septum 124 as a result of the second end 120 of the cannula 116, preventing any further gas or other fluid from traveling through the septum 124. Since the septum 124 is sealed to further gas and other fluid travel, no further fluid will be permitted to escape into the external environment.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
   a closed extravascular system, wherein the system includes a fluid path through a intravenous tube; and
   a gas vent in communication with the fluid path, the gas vent venting gas from the intravenous tube, the gas vent being disposed directly on one of:
   a) the intravenous tube, wherein the gas vent protrudes out from the intravenous tube; and
   b) a port directly connected to the intravenous tube, the port having a body with the fluid path extending therethrough, a septum coupled to the body providing selective access to the fluid path, a gas vent in communication with the fluid path extending through the port;
   wherein the closed extravascular system remains closed after gas vents from the fluid path through the gas vent.

2. The medical device of claim 1, wherein the gas vent includes a venting material and a user-activated rotation valve.

3. The medical device of claim 1, wherein the gas vent includes a user-activated seal with a pull tab.

4. The medical device of claim 1, wherein the gas vent includes at least two layers of fluid seal material separated by a layer of gas.

5. The medical device of claim 1, wherein the gas vent includes a removable filter plug and a reseal elastomer.

6. The medical device of claim 1, wherein the gas vent includes a cannula and a cartridge seal.

7. The medical device of claim 1, wherein the gas vent includes:

a cannula with a first end and a second end,
a venting material secured to the first end of the cannula,
a push shaft with a first end and a second end, and
a septum secured to the second end of the push shaft and in moveable contact with the second end of the cannula.

8. The medical device of claim 1, wherein the gas vent includes a narrow vent hole and a floatable structure, wherein the floatable structure is in the fluid path and in communication with the narrow vent hole.

9. The medical device of claim 1, wherein the gas vent includes a narrow vent hole and a heavy structure capable of sinking in liquid, wherein the heavy structure is in the fluid path and in communication with the narrow vent hole.

10. The medical device of claim 1, wherein the gas vent includes a spring-loaded sealing member.

11. The medical device of claim 1, wherein the gas vent includes a sealing member that expands when the sealing member comes into contact with liquid.

12. The medical device of claim 1, wherein the gas vent includes a check valve.

13. The medical device of claim 1, wherein the gas vent is in direct communication with the fluid path.

14. The medical device of claim 1, wherein the gas vent includes a moisture-cure material.

15. The medical device of claim 1, wherein the gas vent includes a porous membrane.

16. The medical device of claim 1, wherein the gas vent includes
an expandable vent material,
a cannula with a first end and a second end, and
a septum in communication with the second end of the cannula,
wherein the first end of the cannula is anchored within the expandable vent material,
wherein the vent material is capable of expanding and drawing the second end of the cannula through the septum when the vent material is exposed to liquid.

17. A method of venting a medical device, comprising:
providing a closed extravascular system, wherein the extravascular system includes a fluid path through an intravenous tube;
providing a gas vent in communication with the fluid path, the gas vent being disposed directly on one of:
a) the intravenous tube, wherein the gas vent protrudes out from the intravenous tube; and
b) a port directly connected to the intravenous tube, the port having a body with the fluid path extending therethrough, a septum coupled to the body providing selective access to the fluid path, a gas vent in communication with the fluid path extending through the port;
venting gas from the intravenous tube through the gas vent; and
maintaining a closed extravascular system during and after venting.

18. The method of claim 17, further comprising closing the gas vent upon user-activation of the gas vent.

19. The method of claim 17, further comprising saturating a first layer of venting material with liquid.

20. The method of claim 17, further comprising removing the gas vent after venting.

21. The method of claim 17, further comprising closing the gas vent with a floatable structure.

22. The method of claim 17, further comprising closing the gas vent with a heavy structure.

23. The method of claim 17, further comprising closing the gas vent with a spring-loaded sealing member.

24. The method of claim 17, further comprising closing the gas vent with an expandable sealing member.

25. The method of claim 17, wherein providing a gas vent in communication with the fluid path includes providing the gas vent in direct communication with the fluid path.

26. The method of claim 17, further comprising curing a material to form a seal.

27. The method of claim 17, wherein the gas vent includes an expandable vent material, a cannula with a first end and a second end, and a septum in communication with the second end of the cannula;
further comprising:
anchoring the first end of the cannula within the expandable vent material;
expanding the vent material; and
drawing the second end of the cannula through the septum as the vent material expands.

28. A medical device, comprising:
means for providing access to the vascular system of a patient, wherein the means for providing access includes a fluid path; and
means for venting the means for providing access, wherein the means for venting communicates with the fluid path, the means for venting the means for providing access being disposed directly on one of:
a) the intravenous tube, wherein the gas vent protrudes out from the intravenous tube; and
b) a port directly connected to the intravenous tube, the port having a body with the fluid path extending therethrough, a septum coupled to the body providing selective access to the fluid path, a gas vent in communication with the fluid path extending through the port.

* * * * *